United States Patent [19]

Terada et al.

[11] Patent Number: 5,049,663
[45] Date of Patent: * Sep. 17, 1991

[54] PROCESS FOR PRODUCING 1-β-D-ARABINOFURANOSYLCYTOSINE-5'-STEARYLPHOSPHATE MONOSODIUM SALT AND MONOHYDRATE THEREOF

[75] Inventors: Takashi Terada, Yono; Minoru Aoki, Tokyo; Hiroshi Ohtaki, Yono; Manami Morozumi, Choshi, all of Japan

[73] Assignees: Nippon Kayaku Kabushiki Kaisha, Tokyo; Yamasa Shoyu Kabushiki Kaisha, Chiba, both of Japan

[*] Notice: The portion of the term of this patent subsequent to Mar. 14, 2006 has been disclaimed.

[21] Appl. No.: 399,303

[22] Filed: Aug. 25, 1989

Related U.S. Application Data

[60] Continuation-in-part of Ser. No. 124,930, Nov. 24, 1987, which is a division of Ser. No. 28,951, Mar. 23, 1987, Pat. No. 4,812,560.

[30] Foreign Application Priority Data

Mar. 24, 1986 [JP] Japan .................................. 61-63963
May 21, 1986 [JP] Japan ................................ 61-114680

[51] Int. Cl.⁵ ........................ C07H 19/10; C07H 1/00
[52] U.S. Cl. ........................................ 536/29; 536/28
[58] Field of Search .................................. 536/28, 29

[56] References Cited

U.S. PATENT DOCUMENTS 4,542,021 9/1985 Kodama et al. .
4,812,560 3/1989 Terada et al. ......................... 536/29

FOREIGN PATENT DOCUMENTS 0239015 3/1987 European Pat. Off. .
2250763 6/1975 France .
52-89681 7/1977 Japan .
0129299 10/1980 Japan .................................... 536/28

OTHER PUBLICATIONS

Soneyoshi et al., Chem. Phar. Bull., 28(10), 2915–2923.
Chemical Abstract 88:23342u, Morozumi et al., Japan, Kokai 77-89681, Jul. 27, 1977 (Yamasa Shoyo Co Ltd).

*Primary Examiner*—Herbert J. Lilling
*Attorney, Agent, or Firm*—John P. White

[57] ABSTRACT

Disclosed herein are a novel process for producing 1-β-D-arabinofuranosylcytosine-5'-stearylphosphate monosodium salt, which has been expected as an oral antitumor agent, and 1-β-D-arabinofranosylcytosine-5'-stearylphosphate monosodium salt monohydrate obtained from the above-mentioned monosodium salt.

3 Claims, 2 Drawing Sheets

β-type
angle of diffraction (2θ)

γ-type
angle of diffraction (2θ)

amorphous
angle of diffraction (2θ)

β-type

γ-type amorphous

PROCESS FOR PRODUCING 1-β-D-ARABINOFURANOSYLCYTOSINE-5'-STEARYLPHOSPHATE MONOSODIUM SALT AND MONOHYDRATE THEREOF

This is a continuation-in-part application of U.S. Ser. No. 124,930, filed Nov. 24, 1987 now abandoned, which is a divisional application of U.S. Ser. No. 028,951, filed Mar. 23, 1987, now U.S. Pat. No. 4,812,560, issued Mar. 14, 1989.

BACKGROUND OF THE INVENTION

The present invention relates to a process for producing 1-β-D-arabinofuranosylcytosine-5'-stearylphosphate monosodium salt which is excellent in stability and 1-β-D-arabinofuranosylcytosine-5'-stearylphosphate monosodium salt monohydrate which is nonhygroscopic and is excellent in stability.

A process for producing 1-β-D-arabinofuranosylcytosine-5'-stearylphosphate sodium (hereinafter referred to as Ara-C-5'-stearylphosphate sodium salt) has been disclosed in Japanese Patent Publication No. 55-49588 (1980) According to the disclosed process, after adjusting an aqueous solution of Ara-C-5'-stearylphosphate (a free acid) to pH of 7.0 by sodium hydroxide, the thus adjusted aqueous solution is condensed and ethanol was added to the condensate, thereby precipitating Ara-C-5'-stearylphosphate sodium salt.

Ara-C-5'-stearylphosphate sodium salt obtained by the process disclosed in Japanese Patent Publication No. 55-49588 (1980) is a powdery substance and does not show any definite diffraction peaks on X-ray diffraction, namely, it is an amorphous substance (refer to FIG. 3).

In the case where Ara-C-5'-stearylphosphate sodium salt obtained by the above conventional process was left for 14 months under the conditions of a temperature of 25° C. and a relative humidity (RH) of 75%, the content thereof was reduced to 93.7% by weight of the initial value and in the case where left for 3 months under the conditions of a temperature of 50° C. and an RH of 74%, the content thereof was remarkably reduced to 58.6% by weight of the initial value, and it was ascertained that 1β-D-arabino- furanosyluracil-5'-stearylphosphate sodium salt was formed as a decomposition product.

Furthermore, in the case where Ara-C-5'-stearylphosphate sodium salt was left under the condition of a temperature of 25° C. and an RH of 93%, the weight thereof increased by 12 to 13%, namely the sodium salt shows a remarkably high hygroscopicity.

The above-mentioned facts show that when the Ara-C-5'-stearylphosphate sodium salt obtained by the publicly known process is prepared into a medical product, particular consideration of the hygroscopicity thereof should be given and also a strict packaging of the product is necessary to prevent the product from taking up water when the product is put into market. In addition to the above, since the Ara-C-5'-stearylphosphate sodium salt is poor in stability and the activity in the preparation including the compound as an active ingredient is reduced by the decomposition in very short time, such a preparation cannot be actually put into market.

As a result of the present inventors' studies for providing a novel process for producing Ara-C-5'-stearylphosphate monosodium salt which is stable and suitable for producing medicines, it has been found by the present inventors that a stable Ara-C-5'-stearylphosphate monosodium salt can be obtained by adjusting an aqueous solution or suspension of Ara-C-5'-stearylphosphate to pH 9.7 to 13 by sodium hydroxide and further that by transforming the thus obtained monosodium salt into Ara-C-5'-stearylphosphate monosodium salt monohydrate represented by the following formula:

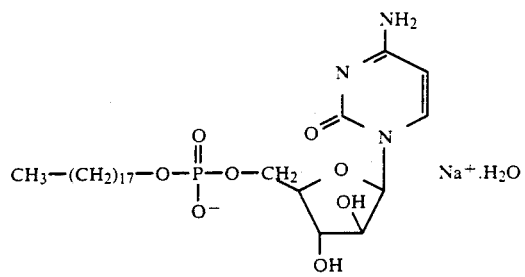

under a specified condition, it can be possible to obtain a compound which is nonhygroscopic and is excellent in stability.

On the basis of the findings, the present inventors have completed the present invention.

SUMMARY OF THE INVENTION

In the first object of the invention, there is provided a process for producing Ara-C-5'-stearylphosphate monosodium salt, comprising the steps of adjusting an aqueous solution or suspension of Ara-C-5'-stearylphosphite to pH 9.7 to 13 by sodium hydroxide, and isolating the thus formed Ara-C-5'-stearylphosphate monosodium salt.

In the second object of the invention, there is provided an Ara-C-5'-stearylphosphate monosodium salt monohydrate.

In the third object of the invention, there is provided a process for producing Ara-C-5'-stearylphosphate monosodium salt monohydrate, comprising the steps of adjusting the aqueous solution or suspension of Ara-C-5'-stearylphosphate to pH 9.7 to 13 by sodium hydroxide; adding an organic solvent which is miscible with water to said aqueous solution or suspension, thereby precipitating Ara-C-5'-stearylphosphate monosodium salt;

(A) stirring the thus resulted mixture on continued heating, isolating the thus formed crystals of the monohydrate from the mixture; or (B) isolating the thus precipitated monosodium salt,
(1) suspending the thus isolated monosodium salt in an organic solvent which is miscible with water, isolating the thus formed crystals from the aqueous suspension, or
(2) thermally dissolving the thus isolated monosodium salt in an organic solvent which is miscible with water and cooling the thus formed solution, isolating the thus formed crystals from the aqueous solution, and then drying the isolated crystals at a temperature of not higher than 100° C.

BRIEF EXPLANATION OF THE DRAWINGS

Of the attached drawings, FIG. 1 shows that of the crystals of β type and FIG. 2 shows that of the crystals of γ type.

Moreover, FIG. 4 shows that of the crystals of β type and FIG. 5 shows that of the crystals of γ type.

DETAILED DESCRIPTION OF THE INVENTION

Ara-C-5'-stearylphosphate monosodium salt according to the present invention takes the following three forms according to the process for producing the monosodium salt.

Namely, the monosodium salt separated from the aqueous solution or suspension of Ara-C-5'-stearylphosphate adjusted to pH 9.7 to 13 is amorphous (α type) and the monohydrate of monosodium salt can take the two crystal forms, namely β type and γ type, and the present invention includes any of them.

The ratio of sodium to one mol of Ara-C-5'-stearylphosphate in Ara-C-5'-stearylphosphate monosodium salt according to the present invention is not less than 0.95 mol, preferably not less than 0.99 mol, namely, nearly agrees with the stoichiometric amount. As compared with the above, the ratio of sodium to one mol of Ara-C-5'-stearylphosphate in Ara-C-5'-stearylphosphate sodium salt obtained by the conventional process is about 0.75 mol. Accordingly, Ara-C-5'-stearylphosphate sodium salt obtained by the conventional process contains a considerable amount of the free acid, Ara-C-5'-stearylphosphate, and it is considered that the high content of the free acid is the cause of the high hygroscopicity and the instability of sodium salt obtained by the conventional process.

The β type and γ type crystals of Ara-C-5'-stearylphosphate monosodium salt monohydrate according to the present invention have the following physical and chemical properties.

X-RAY DIFFRACTION PATTERN OF THE CRYSTALS

Figure 1:
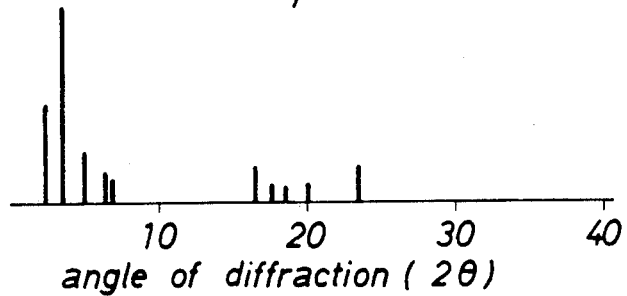
FIGS. 1 and 2 are the X-ray diffraction patterns of Ara-C-5'-stearylphosphate monosodium salt monohydrate.
Figure 2:
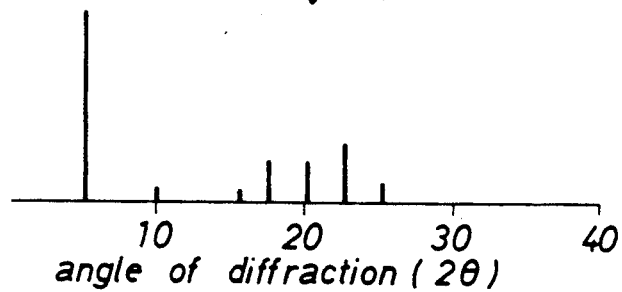
Figure 3:
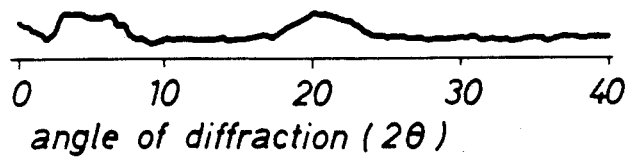
FIG. 3 shows an X-ray diffraction pattern of the amorphous Ara-C-5'-stearylphosphate sodium salt obtained by the publicly known process.

The X-ray diffraction patterns of the crystals, obtained by an X-ray diffraction apparatus (made by RIGAKU-DENKI Co.) provided with a Cu X-ray tube with a nickel foil filter and a scintillation counter, were shown in FIG. 1 (β type) and FIG. 2 (γ type), and the results of analysis of the patterns are shown in Table 1.

TABLE 1

| Type | d(Å) | I/I₁ |
|---|---|---|
| β type | 23.86 | 1 |
|  | 17.31 | 0.25 |
|  | 12.99 | 0.22 |
|  | 12.27 | 0.15 |
|  | 5.37 | 0.23 |
|  | 4.39 | 0.15 |
|  | 3.75 | 0.27 |
| γ type | 18.02 | 1 |
|  | 8.93 | 0.07 |
|  | 4.98 | 0.14 |
|  | 4.48 | 0.21 |
|  | 3.95 | 0.20 |

Note: Cu:Ni, 30 kV, 20 mA, λ = 1.5405 Å

THERMAL ANALYSIS

Figure 4:
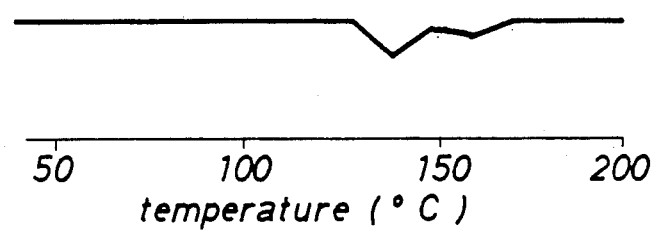
FIGS. 4 and 5 are the thermogram of differential thermal analysis of Ara-C-5'-stearylphosphate monosodium salt monohydrate.
Figure 5:
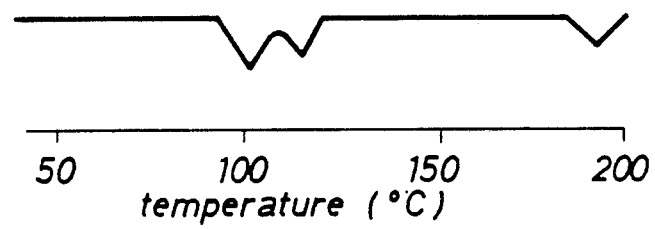
Figure 6:
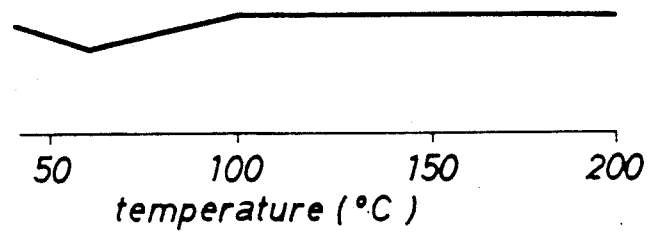
FIG. 6 shows that of the amorphous Ara-C-5'-stearylphosphate sodium salt obtained by the publicly known process.

As the results of the differential thermal analysis by a thermal analytical apparatus made by SHIMAZU Works (type: DT-30), the β type absorbed heat at 128° C., and the γ type absorbed heat at 98° C. and 113° C., the phenomenon showing the dehydration of crystal water from the specimen. As the results of thermogravimetric analysis, 3% of weight reduction was observed in β type and also in γ type. The thermograms of differential thermal analysis of the specimens are shown in FIG. 4 (β type) and FIG. 5 (γ type).

MOISTURE-CONTENT OF THE CRYSTALS

As a result of measurement of moisture-content of both the crystals by the Karl Fischer's method, the moisture content of the β type crystals was 3.0% and that of the γ type crystals was 2.92%, the data agreeing will with the theoretical value of 2.92% calculated from the molecular formula of $C_{27}H_{49}N_3NaO_8P \cdot H_2O$.

The stable Ara-C-5'-stearylphosphate monosodium salt according to the present invention can be obtained by the following process.

(A) Production of the stable Ara-C-5'-stearylphosphate monosodium salt

The stable Ara-C-5'-stearylphosphate monosodium salt can be obtained by adjusting an aqueous solution or suspension of Ara-C-5'-stearylphosphate to pH 9.7 to 13 by sodium hydroxide, then, isolating the monosodium salt from the thus adjusted solution.

As the aqueous solution or suspension of Ara-C5'-stearylphosphate, in addition to the solution prepared by dissolving or suspending Ara-C-5'-stearylphosphate into an aqueous solvent, any of the aqueous solution or suspension containing Ara-C-5'-stearylphosphate such as a solution or suspension prepared by dissolving or suspending Ara-C-5'-stearylphosphate sodium salt containing Ara-C-5'-stearylphosphate into an aqueous solvent, etc. can be also used.

As the aqueous solvent, water or a mixed solvent of water and an organic solvent which is miscible with water may be usable. As the organic solvent which is miscible with water, lower alcohols such as methanol, ethanol and propanol, ketones such as acetone and methyl ethyl ketone and cyclic ethers, preferably, a cyclic ether having five- or six-membered ring such as tetrahydrofuran and dioxane may be mentioned.

Although the mixing ratio of the organic solvent to water is not particularly restricted, the mixing ratio of the organic solvent is preferably lower than about 50% by volume based on the mixed solvent.

The amount of water used for dissolving or suspending Ara-C-5'-stearylphosphate is 0.5 to 10 parts by weight, preferably from 0.8 to 5 parts by weight to 1 part by weight of Ara-C-5'-stearylphosphate.

The range of pH of the aqueous solution or suspension which is to be adjusted by sodium hydroxide may be 9.7 to 13, preferably 10.0 to 12.5.

Moreover, although solid sodium hydroxide or an aqueous solution of sodium hydroxide can be used in adjustment of pH of the aqueous solution or suspension of Ara-C-5'-stearylphosphate, it is preferable to use the aqueous solution because the adjustment is easily carried out.

The adjustment of pH of the aqueous solution or suspension can be carried out under an optimal temperature condition, preferably at a temperature of lower than 50° C. The formation of Ara-C-5'-stearylphosphate monosodium salt by the pH-adjustment is finished instantaneously because the reaction is neutralization.

The isolation of the stable Ara-C-5'-stearylphosphate monosodium salt according to the present invention can be carried out according to the conventional method. For instance, a method in which the reaction liquid is condensed to dryness to obtain the monosodium salt, a method in which the condensed reaction liquid is cooled to precipitate the monosodium salt or a method in which the above-mentioned water-miscible organic solvent is added to the reaction liquid to precipitate the monosddium salt may be exemplified. The thus precipitated monosodium salt is collected by filtration and dried.

The water-miscible organic solvent may be added into the reaction liquid in an amount sufficient for precipitating the monosodium salt, and the solvent is usually added in an amount of not less than two times, preferably 3 to 5 times of the amount of water in the reaction liquid.

(B) Production of Ara-C-5'-stearylphosphate monosodium salt monohydrate

The monosodium salt in wet state obtained by isolating from the reaction liquid of Ara-C-5'-stearylphosphate and sodium hydroxide as described above is suspended in the above-mentioned water-miscible organic solvent, preferably in ethanol, in an amount of 3 to 5 times by weight of the monosodium salt, and after stirring the thus prepared mixture for 10 min or more, preferably for 30 min or more, and more preferably for 2 to 6 hours at a temperature of 30 to 90° C., preferably 50 to 70° C., the thus formed crystals are collected and dried at a temperature of not higher than 100° C., preferably 10 to 100° C. to obtain the $\beta$ type crystals of Ara-C-5'-stearylphosphate monosodium salt monohydrate.

The $\beta$ type crystals are also available by the steps of adding the above mentioned water-miscible organic solvent, preferably ethanol, to the high concentrated reaction liquid of Ara-C-5'-stearylphosphate and sodium hydroxide, then stirring the thus resulted mixture on continued heating at a temperature of 30 to 90° C., isolating the thus formed crystals and drying the isolated crystals The $\gamma$ type crystals of Ara-C-5'-stearylphosphate monosodium salt monohydrate are available by the steps of dissolving the $\beta$ type crystals in a water-miscible organic solvent, preferably methanol or ethanol, by heating preferably to a temperature of 30 to 70° C., more preferably 40 to 60° C. and slowly cooling the thus formed solution, thereby precipitating the crystals. The $\gamma$ type crystals are also available by the steps of drying under a reduced pressure the monosodium salt in wet state obtained by isolating from the reaction liquid of Ara-C-5'-stearylphosphate and sodium hydroxide, then dissolving the thus dried monosodium salt in a water-miscible organic solvent, preferably methanol by heating to, for instance, a temperature of about 30 to about 60° C., preferably about 60° C., slowly cooling the thus formed solution, thereby precipitating the crystals, collecting the thus precipitated crystals and drying the thus collected crystals at a temperature of not higher than 100° C. under a reduced pressure.

In addition, Ara-C-5'-stearylphosphate which is the starting material for the stable Ara-C-5'-stearylphosphate monosodium salt according to the present invention and the monohydrate thereof can be obtained by publicly known processes, for instance, the processes disclosed in Japanese Patent Publication No. 55-49588 (1980).

Ara-C-5'-stearylphosphate monosodium salt obtained by the process according to the present invention is excellent in stability, and the monohydrate of the monosodium salt is nonhygroscopic and is stable, and accordingly both compounds are suitable for producing the medicines.

The present invention will be explained more in detail while referring to the following non-limitative Examples.

EXAMPLE 1

Into 1.5 liters of water 500 g of Ara-C-5'-stearylphosphate were added and after adjusting the pH of the mixture to 10.8 by sodium hydroxide while stirring the mixture, 6 liters of ethanol were added to the mixture. After standing the mixture to cool for 16 hours, the thus formed precipitate was collected by centrifugation to obtain Ara-C-5'-stearylphosphate monosodium salt in wet state.

By drying the thus obtained wet salt at 30° C. under a reduced pressure, 332 g of amorphous ($\alpha$ type) Ara-C-5'-stearylphosphate monosodium salt of m.p. 223° C. (decomposition) were obtained The purity of the thus obtained product was 99.5% according to liquid chromatography and $E_1\ _{cm}^{1\%}$ (273 nm, 0.1N NaOH) was 152.3.

The same result as above was obtained when acetone, methyl ethyl ketone, tetrahydrofurane or dioxane was added instead of ethanol to precipitate the monosodium salt.

EXAMPLE 2

To 2.40 g of Ara-C-5'-stearylphosphate (a dried material) 6 ml of water were added and after adjusting the mixture to pH 12.0 with aqueous 1N solution of sodium hydroxide, 30 ml of ethanol were added to the mixture and the mixture was stirred for 3 hours at 55° C. After cooling the mixture for 16 hours by standing, the precipitate was collected by filtration and dried for 10 hours at 30° C. under a reduced pressure to obtain 1.83 g of Ara-C-5'-stearylphosphate monosodium salt ($\alpha$ type) of m.p. 220° C. (decomposition). The purity of the thus obtained product was 99.5% according to liquid chromatography and $E_1\ _{cm}^{1\%}$ (273 nlm, 0.1N NaOH) was 150.9.

EXAMPLE 3

To 2.40 g of Ara-C-5'-stearylphosphate 10 ml of water were added and after adjusting the mixture to pH 10.0 by sodium hydroxide while stirring the mixture, the thus formed solution was condensed to dryness under a reduced pressure to obtain 2.30 g of Ara-C-5'-stearylphosphate monosodium salt ($\alpha$ type).

The melting point of the thus obtained product was 219.8° C. (decomposition), the purity thereof was 99.1% by liquid chromatography and $E_1\ _{cm}^{1\%}$ (273 nm, 0.1N NaOH) was 152.6.

EXAMPLE 4

To 6.4 g (10 mmol) of $N^4, O^{2'}, O^{3'}$-triacetyl-Ara-C-5'-phosphate tri-n-butyl ammonium salt, 5 g of stearyl alcohol, 30 ml of pyridine and 8 g of p-toluenesulfonyl chloride were added and the mixture was maintained at 40° C. for 3 hours. Then, the reaction mixture was extracted after adding 50 ml of water and 50 ml of chloroform.

Deacetylation of the triacetyl compound in the chloroform solution was carried out by adding 20 ml of aqueous ammonia and ethanol thereto and the deacetylate was extracted with water.

After collecting the aqueous layer, the aqueous layer was adjusted to pH 2.5 by adding conc. hydrochloric acid, and the precipitated Ara-C-5'-stearylphosphate was collected by filtration. After adding 20 ml of water to the thus obtained precipitates and adjusting the solution to pH 10.5 by an aqueous 1N solution of sodium hydroxide, 80 ml of ethanol were added to the solution. By collecting the generated precipitate through filtration, Ara-C-5'-stearylphosphate monosodium salt ($\alpha$ type) was obtained in wet state, and by drying the wet material in the same manner as in Example 2, 4.20 g of Ara-C-5'-stearylphosphate monosodium salt ($\alpha$ type) of m.p. 221° C. (decomposition) were obtained.

The purity of the thus obtained product was 99.62% by liquid chromatography and $E_{1\ cm}^{1\%}$ (273 nlm, 0.1N NaOH) was 151.4.

EXAMPLE 5

After adding 50 ml of water to 10 g of Ara-C-5'-stearylphosphate obtained in the same manner as in Example 4, sodium hydroxide was added to adjust the mixture to pH 10.5 while stirring the mixture.

After stirring the mixture for 30 min, 120 ml of 95% ethanol were added to the mixture to precipitate the monosodium salt and the precipitated monosodium salt was collected by filtration.

The thus collected monosodium salt in wet state (moisture-content, about 20% by weight) amounting to 8.5 g was suspended in 30 ml of ethanol and after stirring the suspension for 90 min, the thus treated suspension was subjected to filtration to obtain crystals. The thus obtained crystals were dried at 40° C. under a reduced pressure to obtain Ara-C-5'-stearylphosphate monosodium salt monohydrate (crystals of $\delta$ type) of m.p. 221° C. (decomposition).

The results of X-ray diffraction analysis of the thus obtained product are shown in FIG. 1 and Table 1, and the result of differential thermal analysis of the product is shown in FIG. 4.

EXAMPLE 6

The monosodium salt in wet state obtained in Example 5 was dried for 16 hours at 60° C. under a reduced pressure. Six grams of the thus dried product were dissolved in 20 ml of methanol by heating to 60° C., and after completely dissolving the product, the thus formed solution was slowly cooled to precipitate the crystals and the crystals were collected by filtration and dried at 60° C. under a reduced pressure to obtain the $\gamma$ type crystals of Ara-C-5'-stearylphosphate monosodium salt monohydrate of m.p. 226° C (decomposition). The results of X-ray diffraction analysis of the thus obtained crystals are shown in FIG. 2 and Table 1, the results of differential thermal analysis thereof being shown in FIG. 5.

EXAMPLE 7

To 10 g of Ara-C-5'-stearylphosphate, 30 ml of water were added and after adjusting the pH of the mixture to 10.5 by 5N sodium hydroxide, 50 ml of ethanol were added to the thus formed solution with stirring at about 40° C to precipitate the monosodium salt.

The mixture was heated to 65° C. and after adding the seed crystal of Ara-C-5'-stearylphosphate monosodium salt monohydrate ($\beta$ type), the mixture was maintained with stirring while keeping the temperature for 5 hours to form crystals. After microscopically confirming the completion of crystallization, 20 ml of ethanol were added to the mixture and the mixture was gradually cooled.

After one night, the crystals were filtrated and by drying under a reduced pressure 8.9 g of Ara-C-5'-stearylphosphate monosodium salt monohydrate (crystals of $\beta$ type) of m.p. 220° C. (decomposition) were obtained.

The purity of the thus obtained product was 99.7% by liquid chromatography and $E_{1\ cm}^{1\%}$ (273 nm, 0.1N NaOH) was 153.0.

TEST EXAMPLE 1

The excellent stability of Ara-C-5'-stearylphosphate monosodium salt obtained by the process according to the present invention is explained by the following experiment.

1. Specimen

A. Product of the present invention

Ara-C-5'-stearylphosphate monosodium salt obtained in Example 1.

B. Product of the present invention

Ara-C-5'-stearylphosphate monosodium salt obtained in Example 2.

C. Comparative specimen

Ara-C-5'-stearylphosphate sodium salt produced by the process disclosed in Japanese Patent Publication No. 55-49588 (1980).

2. Test method

Each 1 g of the products of the present invention (Specimens A and B) and the comparative specimen (Specimen C) in a weighing bottle was allowed to stand for 14 months at 25° C. and for 3 months at 50° C. respectively over a saturated NaCl solution in a desiccator (RH of 74 to 76%), and the amount of Ara-C-5'-stearylphosphate monosodium salt in the specimen before and after storage, and the content of the decomposition product in the specimen were measured.

3. Test results

The results of measurement before and after storage are shown in Table 2.

TABLE 2

| Specimen | 25° C. and RH of 76% | | 50° C. and RH of 74% | |
|---|---|---|---|---|
| | before test | after 14 mon. | before test | after 3 mon. |
| A (present invention) | 100.0 (0.0) | 100.0 (0.0) | 100.0 (0.0) | 100.0 (0.0) |
| B (present invention) | 100.0 (0.0) | 100.0 (0.0) | 100.0 (0.0) | 100.0 (0.0) |
| C (comparison) | 100.0 (0.0) | 93.7 (6.3) | 100.0 (0.0) | 58.6 (41.4) |

Note: the numeral value within the parentheses shows the rate of decomposition.

As are shown in Table 2, the monosodium salt according to the present invention did not decompose after storage for 14 months at 25° C. and RH of 76% and also after storage for 3 months at 50° C. and RH of 74%, and therefore the monosodium salt according to the present invention was stable. On the other hand, the reduction of the content was observed in the comparative specimen under the same conditions as above, and also it was found that the reduction of the content was remarkable particularly after standing at 50° C. and RH of 74%.

TEST EXAMPLE 2

The hygroscopicity and the stability upon storage of Ara-C-5'-stearylphosphate monosodium salt monohydrate ($\beta$ type crystals and $\gamma$ type crystals) were tested as follows.

Hygroscopicity

The $\beta$ type crystals dried at 50° C. under a reduced pressure of 5 mmHg and also the Y type crystals dried under the same conditions as above were stored under the conditions of a temperature of 25° C. and RH of 93% for 3 days, however, any change in the weight was not observed both in the $\beta$ type and $\gamma$ type. Namely, both the crystals are non-hygroscopic.

Test for stability in storage (severe test for stability)

Ara-C-5'-stearylphosphate monosodium salt monohydrate ($\beta$ type and $\gamma$ type) was stored for one month at 65° C. and RH of 73%, and the content after storage was measured.

As a result, the content after storage of both the $\beta$ type crystals and the $\gamma$ type crystals was 99.9% which was the same as the value before storage. Namely, Ara-C5'-stearylphosphate monosodium salt monohydrate scarcely decomposed and was very stable.

EXAMPLE 8

(1) Production of Ara-C-5'-stearylphosphate (free acid)

Into 112 ml of a chloroform solution containing 35 mmol of $N^4$, 2', 3'-O-triacetyl-Ara-C-5'-phosphate tri-n-butyl ammonium salt, were added 21 g (69.5 mmol) of 2,4,6-triisopropylbenzenesulfonyl chloride (TPS-Cl) and 18.9 g (69.9 mmol) of stearyl alcohol. After the completion of dissolving, the solution was evaporated to dryness. The residue was dissolved in 70 ml of pyridine, then the solution was subjected to the reaction of 50° C. for 15 hours.

Into the reaction mixture, was poured 700 ml of water, then, the separated precipitate was filtered off.

The filtrate was subjected to distribution procedure after addition of 200 ml chloroform. The extraction was repeated after adding 150 ml chloroform into the water layer. The combined chloroform layer was added with 70 ml of 28% aqueous ammonia and 120 ml ethanol, and the solution was subjected to the deacylation reaction at room temperature for 14 hours.

The reaction mixture was added with 600 ml water and 100 ml ethanol, then, subjected to distribution procedure. The distribution procedure was further repeated twice by adding 200 ml chloroform and 50 ml ethanol.

The water layer was adjusted to pH 1.6 by adding 134 ml of 6N hydrochloric acid. The precipitated Ara-C-5'-stearylphosphate (free acid) was collected by filtration, dissolved in water, then the solution was adjusted to pH 7.0 with 2.8 ml of 7.5N aqueous solution of sodium hydroxide. The solution was allowed tow arm to 40° C., then, adjusted to pH 1.6 with 4 ml of 6N hydrochloric acid, thereby forming precipitate. The precipitate was collected by filtration and washed to obtain Ara-C-5'-stearylphosphate (free acid).

(2) Production of Ara-C-5'-stearylphosphate monosodium salt monohydrate

The free acid obtained above was added with water and sodium hydroxide to adjust the solution to pH 7. The thus adjusted solution was 120 ml in volume. The solution was concentrated to 60 ml under reduced pressure.

Into 20 ml of the solution of pH 7 obtained above, was added 1N aqueous solution of sodium hydroxide to adjust the pH to 10.6. The solution was added with 100 ml ethanol and allowed to warm to dissolve the formed turbidity.

The solution was seeded with crystals of Ara-C-5'-stearylphosphate monosodium salt monohydrate ($\beta$-type) and crystallization was induced at room temperature. The precipitated crystals were collected by filtration, washed with ethanol and dried under reduced pressure to obtain 1.91 g of crystalline powder of Ara-C-5'-stearylphosphate monododium salt monohydrate ($\beta$-type) having a melting point of 218° C.

COMPARATIVE EXAMPLE 1

Into 20 ml of the same solution of pH 7 as in Example 8, was added 100 ml ethanol with stirring, and the solution was cooled to 2° C. The separated precipitate was collected by filtration, washed with ethanol and dried under reduced pressure to obtain 3.28 g of amorphous powder of Ara-C-5'-stearylphosphate monosodium salt.

The properties of the monohydrate of Example 8 and the monosodium salt of Comparative Example 1 are shown in Table 3 below.

TABLE 3

|  | Example 8 | Comparative Example 1 |
|---|---|---|
| L.O.D.[1] | 3.37% | 3.12% |
| mp(°C.) (decomposition) | 218 | 195 |
| pH[2] | 10.68 | 8.15 |
| DTA[3] (heat absorption peak) (°C.) | 113,161 | (110) vague |
| Na content[4] | 108% | 70% |

[1] Weight loss on drying (reduced pressure, 120° C., 4 hours)
[2] Measured as a solution in distilled water.
[3] Differential thermal analysis
[4] The ratio (mol %) of the determined amount to the theoretical amount in 100% sodium salt. Determination was carried out by atomic-absorption spectroscopy under the following conditions.
Apparatus: SAS-727 model (Dai-ni Seikousha Co.)
Method: flame analysis
Flame: Air-Acetylene
Sodium standard solution: 0.2, 0.4, 0.6 and 0.8 ppm
Sample solution: A 500 ml solution in deionized water containing 100 mg of sample was prepared. Then, 5 ml of the solution was diluted to 100 ml with deionized water and used as a sample solution.

EXAMPLE 9

The procedure in Example 8 was repeated to obtain $\beta$-type crystals. After dissolving 10 g of $\beta$-type crystals in 50 ml methanol at 50 to 55° C., the solution was stirred for 4 hours, and then, allowed to stand overnight at room temperature. The precipitated crystals were collected by filtration and dried under reduced pressure to obtain 8.58 g of crystalline powder of Ara-C-5'-stearylphosphate monosodium salt monohydrate ($\gamma$-type).

TEST EXAMPLE 3

Each of the products obtained in Example 8 and 9, and Comparative Example 1 was allowed to stand for 10 days, 20 days and 30 days at 50° C. and 75% RH (relative humidity), and for 2 days, 4 days, 7 days, and 14 days at 65° C. and 75% RH, respectively. The amount of Ara-C-5'-stearylphosphate monosodium salt in each tested sample was determined by HPLC.

| HPLC Condition |
| --- |
| Column: Nucleosil 5NH₂ 4 mm ID × 200 mm |
| Column Temperature: 30° C. |
| Mobile phase: Methanol: 0.1M tris buffer, pH 7.0(5:1) |
| Flow rate: 1 ml/min |
| Injection volume: 10 μl |
| Detector: UV 275 nm |

The results are shown in Table 4 below as the ratio of the amount after storage to the amount before storage.

TABLE 4

| | Storage Condition | | | | | | |
| --- | --- | --- | --- | --- | --- | --- | --- |
| | 50° C. 75% RH | | | 65° C. 75% RH | | | |
| | 10 days % | 20 days % | 30 days % | 2 days % | 4 days % | 7 days % | 13 days % |
| Example 8 | 100.2 | 100.1 | 101.1 | 100.4 | 100.7 | 100.7 | 100.3 |
| Example 9 | 99.5 | 99.7 | 100.5 | 100.7 | 99.2 | 100.9 | 102.7 |
| Comparative Example 1 | 96.5 | 92.3 | 87.1 | 95.8 | 86.1 | 80.3 | 55.6 |

What is claimed is:

1. 1-β-D-arabinofuranosylcytosine-5'-stearylphosphate monosodium salt monohydrate having the melting point of about 218 to 226° C. (decomposition), which is represented by the formula:

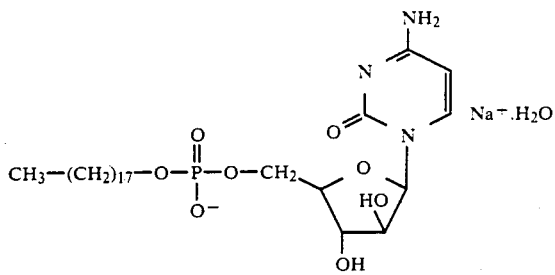

2. 1-β-D-arabinofuranosylcytosine-5'-stearylphosphate monosodium salt monohydrate according to claim 1, wherein said monosodium salt monohydrate is the crystal having the following lattice distance:

| d(Å) | I/I₁ |
| --- | --- |
| 23.86 | 1 |
| 17.31 | 0.25 |
| 12.99 | 0.22 |
| 12.27 | 0.15 |
| 5.37 | 0.23 |
| 4.39 | 0.15 |
| 3.75 | 0.27 | upon X-ray diffraction measured under the conditions of Cu;Ni, 30 kV, 20 mA and λ=1.5405 Å.

3. 1-β-D-arabinofuranosylcytosine-5'-stearylphosphate monosodium salt monhydrate according to claim 1, wherein said monosodium salt monohydrate is the crystal having the following lattice distance:

| d(Å) | I/I₁ |
| --- | --- |
| 18.02 | 1 |
| 8.93 | 0.07 |
| 4.98 | 0.14 |
| 4.48 | 0.21 |
| 3.95 | 0.20 | upon X-ray diffraction measured under the conditions of Cu;Ni, 30 kV, 20 mA and λ=1.5405 Å.

* * * * *